/

US007462360B2

(12) United States Patent
Kim et al.

(10) Patent No.: US 7,462,360 B2
(45) Date of Patent: Dec. 9, 2008

(54) ALLOFERONS—IMMUNOMODULATORY PEPTIDES

(75) Inventors: Soo In Kim, Seoul (KR); Sergey Ivanovich Chernysh, St. Petersburg (RU); German Petrovich Bekker, Essen (DE); Natalia Borisovna Makhaldiani, Moscow (RU); Jules Hoffman, Strasbourg (FR); Philippe Bulet, Vendenhem (FR)

(73) Assignee: Entopharm Co., Ltd., Seoul (KR)

( * ) Notice: Subject to any disclaimer, the term of this patent is extended or adjusted under 35 U.S.C. 154(b) by 563 days.

(21) Appl. No.: 10/742,864

(22) Filed: Dec. 23, 2003

(65) Prior Publication Data
US 2004/0138137 A1    Jul. 15, 2004

Related U.S. Application Data

(62) Division of application No. 09/748,114, filed on Dec. 27, 2000, now Pat. No. 6,692,747.

(30) Foreign Application Priority Data

Dec. 27, 1999   (RU) ................... 99127725

(51) Int. Cl.
A61K 38/08    (2006.01)
A61K 38/10    (2006.01)
A61K 38/16    (2006.01)
A61K 38/03    (2006.01)

(52) U.S. Cl. ................... 424/278.1; 514/12; 514/13; 514/14; 514/15

(58) Field of Classification Search ............... 424/85.1, 424/204.1, 184.1; 514/16; 530/327
See application file for complete search history.

(56) References Cited

U.S. PATENT DOCUMENTS

| 5,480,782 A | 1/1996 | Nonoyama et al. |
| 5,482,711 A | 1/1996 | Medenica |
| 5,714,577 A | 2/1998 | Montelaro et al. |
| 5,804,558 A | 9/1998 | Lehrer et al. |
| 5,827,516 A | 10/1998 | Urban et al. |

FOREIGN PATENT DOCUMENTS

| DE | 4334600 A1 | 4/1995 |
| EP | 0299828 A1 | 1/1989 |
| EP | 0320528 A1 | 6/1989 |
| EP | 0856519 A2 | 8/1998 |
| WO | WO 81/03124 A1 | 11/1981 |
| WO | WO 90/14098 A1 | 11/1990 |
| WO | WO 96/04005 A1 | 2/1996 |
| WO | WO 96/22067 | * 7/1996 |

OTHER PUBLICATIONS

Guo et al (PNAS 101:9205-9210, 2004).*
Bowie et al (Science 247:1306-1310, 1990).*
Trinchieri, G., "Biology of Natural Killer Cells", Advances in Immunology, 1989, pp. 187-376, vol. 47, Academic Press, Inc.
Brittenden, J. et al., "Natural Killer Cells and Cancer", Cancer: Interdisciplinary International Journal of the American Cancer Society; Apr. 1, 1996, pp. 1226-1243, vol. 77, No. 7, John Witey & Sons, Inc.
Bekkering, F. et al., "Ultrarapid Hepatitis C Virus Clearance by Daily High-Dose Interferon in Non-Responders to Standard Therapy" Journal of Hepatology, 1998; pp. 960-964; vol. 28; European Association for the Study of Liver; Denmark, 1998.
Cardamakis, E. et al, Treatment of Recurrent Genital Herpes with Interferon Alpha-2α Gynecol. Obstet Invest., 1998, pp. 54-57, vol. 46, No. S. Karger AG, 1998.
Zee, B. et al, "Quality-Adjusted Time Without Symptoms or Toxicicty Analysis of Interferon Maintenance in Multiple Myeloma", Journal of Clinical Oncology, Aug. 1998, pp. 2834-2839, vol. 16, No. 8, W.B. Saunders Company.
Aviles, A. et al., Maintenance Therapy with Interferon Alfa 2b in Hodgkin Disease, Leukemia and Lymphoma, 1998, pp. 651-656, vol. 30, No. 5/6, Hardwood Academic Publishers.
Gilbert, H., "Long Term Treatment of Myeloproliferative Disease with Interferno-α-2b", Cancer; Interdisiplinary International Journal of the American Cancer Society, Sep. 15, 1998, pp. 1205-1213, vol. 83, No. 6; John Wiley & Sons, Inc.
Durelli, L. et al; "Interferon alpha treatment of relapsing-remitting multiple sclerosis: long-term study of the correlations between clinical and magnetic resonance imaging results and effects on the immune function", Multiple Sclerosis: Clinical and Laboratory Research, Sep. 1994, pp. 32-37, vol. 1, Supplement 1, Stockton Press, Brussels, Belgium.
Schneider, L. et al., "Long-Term Therapy with Recombinant Interferon-gamma (rIFN-y) for Atopic Dermatitis", Annals of Allergy, Asthma & Immunology, Mar. 1998, pp. 263-268, vol. 80, No. 3.
Kullberg, B.J., "Trens in Immunotherapy of Fungal Infections", Eur. J. Clin. Microbiol. Infect. Dis, Jan. 1997, pp. 51-55, vol. 16.
Akaza, H. et al., "Bropirimnie, an orally active Anticancer Agent for Superficial Bladder Cancer", Eur. Urol., Jul. 1998, pp. 107-110, vol. 34, Karger AG, Base!
Naumann; U. et al; "Complete cDNA and Gene Sequence of the Developmentally Regulated Arylphorin of Calliphora Vicina and its Homology to Insect Hemolymph Proteins and Arthropod Hemocyanins", Biochemical and Biophysical Research Communications, Jun. 28, 1991, pp. 963-972, vol. 177, No. 3, Academic Press, Inc.
Russian Ministry of Health Certification No. 002829/01 issued Sep. 22, 2003, for Allokin-alfa.

(Continued)

Primary Examiner—Mary E Mosher
(74) Attorney, Agent, or Firm—Arent Fox LLP

(57) ABSTRACT

The invention belongs to the field of biologically active peptides specifically stimulating antiviral, antimicrobial and antitumor activity of the human and animal immune system.

7 Claims, No Drawings

OTHER PUBLICATIONS

Russian Ministry of Health Certification No. 002830/02 issued Sep. 22, 2003, for Alloferon.

English language Abstract of Russian article: Ershov, F.I., et al., "Allokine-alpha effect on the course of chronic genital herpes relapses"; *Materia Medica*, 2003, No. 4 (40), pp. 103-111.

Russian language article Ershov, F.I., et al., "Allokine-alpha effect on the course of chronic genital herpes relapses"; *Materia Medica*, 2003, No. 4 (40), pp. 103-111.

Chernysh, Sergey, et al., "Antiviral and Antitumor Peptides From Insects", PNAS, Oct. 1, 2002, vol. 99, No. 20., pp. 12628-12632.

\* cited by examiner

ALLOFERONS—IMMUNOMODULATORY PEPTIDES

This application is a divisional of U.S. Ser. No. 09/748,114 filed Dec. 27, 2000, now U.S. Pat. No. 6,692,747. The entire contents of the above-identified application is hereby incorporated by reference. This application claims priority to RU 99127725 filed Dec. 27, 1999, the entirety of which is hereby incorporated by reference.

The present invention is concerned with immunomodulatory materials of natural origin. In particular, the present invention is concerned with peptides of invertebrate origin and pharmaceutical preparations comprising such peptides which are useful in the treatment of immune deficient conditions, infections and oncological diseases.

In the state of the art various pharmaceutical preparations of natural origin containing materials of animal, including insect, and plant tissues able to stimulate the immune system's efficacy are known.

A process for obtaining cellular protein having anti-HIV activity from CD4-positive T cells or myeloid cells is disclosed in U.S. Pat. No. 5,480,782.

A topic formulation comprising a Ginkgo biloba extract exhibiting antibacterial and antiviral properties is disclosed in DE 43 34 600 A1.

WO 96/04005 discloses a pharmaceutical composition for stimulation of the immune response of an organism comprising as the active ingredient major histocompatibility complex antigens extracted from animal tissues, serum or cells. The tissues, cells or sera are chosen from goat, veal or pig liver and bovine red blood cells.

A pharmaceutical composition containing an extract of the plant *Nigella saliva* is disclosed in U.S. Pat. No. 5,482,711 for treating cancer, preventing the side effects of anticancer chemotherapy, and for increasing the immune functions in humans.

WO 81/03124 discloses a polypeptide fraction isolated from the mussel *Mytilus edulis* and used as antibiotic composition effective against various viruses, bacteria and protozoa.

Antibacterial peptides from honey bees and a process for their isolation, production and applications have been disclosed in EP 0 299 828 A1.

Antibacterial peptides isolated from the Coleopteran insects, *Tenebrio molitor* and *Leptinotarsa decemineata* are disclosed in WO 90/14098.

Antibacterial protein isolated from the Lepidopteran insect, *Hyalophora gloveri* is disclosed in EP 0 856 519 A2.

Antimicrobial peptides structurally similar with arginine-containing fragments of lentivirus transmembrane proteins are disclosed in U.S. Pat. No. 5,714,577.

Antiviral and antimicrobial peptides isolated from porcine leucocytes are disclosed in U.S. Pat. No. 5,804,558.

Immunomodulatory peptides specifically binding major histocompatibility complex class II antigens and decreasing in that way a possibility of autoimmune disease are disclosed in U.S. Pat. No. 5,827,516.

EP 0 320 528 A1 discloses the use of hemocyanins and arylphorins isolated from various molluscs and arthropods including the insect *Calliphora erythrocephala* as stimulants the production of specific antibodies and the antitumor activity of antibody-dependent T-lymphocytes.

The preparations mentioned above and analogous natural pharmaceutical preparations enhance the recent arsenal of medicines suitable for treatment of immune deficient conditions, infections and oncological diseases. However, the pharmaceuticals which are available up to now do not cover existing demands in immunomodulatory medicines.

Therefore, it is an object of the present invention to provide a pharmaceutical preparation having immunomodulatory activity and in particular being useful for the treatment of immune deficient conditions, infections and oncological diseases.

It has now surprisingly been found that specific peptides exhibit the desired immunomodulatory activity.

Thus, the present invention relates to a peptide consisting of up to 30 amino acid residues and having the following general structural formula (1) (SEQ ID NO: 31):

$$X_1\text{-His-Gly-}X_2\text{-His-Gly-Val-}X_3 \quad (1)$$

wherein $X_1$ is absent or represents at least one amino acid residue, $X_2$ is a peptide bound or represents at least one amino acid residue, and $X_3$ is absent or represents at least one amino acid residue, or a pharmaceutically acceptable salt or ether thereof, the peptide exhibiting immunomodulatory activity.

The present invention provides a new class of immunomodulatory peptides, designated "alloferons" herein, representative members of which were isolated from the blood of bacteria challenged larvae of an insect, blow fly *Calliphora vicina* R.-D. (Diptera, Calliphoridae).

The alloferons of the invention have been found to stimulate cytotoxic anticancer activity of animal (mouse) and human natural killer cells. Experimental data on the alloferons' immunomodulatory activity show that they are able to stimulate the cytotoxic anticancer activity of human and mouse lymphocytes at extreme low concentrations. The minimum effective concentration was determined to be about 0.0005 nanogram/ml. The optimum concentration was found to be 0.05-0.5 nanogram/ml. Assuming the important role of natural cytotoxicity as effector mechanism of innate immunity (Trinchieri G., Advances in Immunology, 1989, vol. 47, 187-375; Brittenden J., Heys S. D., Ross J. and Eremin O., 1996, vol. 77, 1126-1243), alloferons may be useful as antiviral, antimicrobial and anticancer medicines of immunomodulatory mode of action.

Moreover, with regard to the stimulation of the anticancer activity of the cytotoxic lymphocytes, alloferons were found to induce intensive and prolonged interferon synthesis in experimental animals. Interferons are a group of key antiviral (alpha- and beta-interferons) and immunomodulatory (gamma-interferon) cytokins produced in the organism in response to viral infection and some other external stimuli. Elevation of interferons concentration in the blood helps to cure or mitigate a broad range of viral, oncological and autoimmune disorders. Injections of recombinant or natural interferons are successfully used in the immunotherapy of hepatitis C (Bekkering et al., J. Hepathology, 1998, 28, 6, p. 960-964), herpes (Cardamakis et al., Gynecol. Obstet. Invest., 1998, 46, 1, p. 54-57), multiple myeloma (Zee et al., J. Clin. Oncol., 1998, 16, 8, p. 2834-2839), Hodgkin's disease (Aviles et al., Leuk. Lymphoma, 1998, 30,5-6, p. 651-656), myeloid leukemia (Gilbert H. S., Cancer, 1998, 83,6,p. 1205-13), multiple sclerosis (Durelli et al., Mult. Scler, 1995,1, suppl.1, p. 32-37), atopic dermatitis (Schneider et al., Ann. Allergy Asthma Immunol., 1998, 80, 3, p. 263-268), fungal infections (Kullberg, Eur. J. Clin. Microbiol. Infect. Dis., 1997, 16, p. 51-55) etc. Moreover exogenic interferons, inducers of endogenic interferon synthesis such as bropirimine, a phenylpyrimidinone analog, might be used to achieve similar therapeutic results (Akaza et al., Eur. Urol., 1998, 34, p. 107-110).

Experimental data show that alloferons effectively induce interferon synthesis and stimulate some immunological reactions (natural killers activity) in a manner similar to interferons. Therefore alloferons are believed to have similar therapeutic use compared to interferons and interferon inducers including but not limited to treatment of interferon-sensitive viral and cancer diseases. Direct confirmation of this hypothesis is obtained in experiments with virus infected mice. It is shown that alloferon administration significantly increase the survival rate in mice intrapulmonary infected with a lethal dose of human influenza virus A and B.

where:

$X_1$ is absent or represents at least one amino acid residue $X_2$ is a peptide bond or represents at least one amino acid-residue, and $X_3$ is absent or represents at least one amino acid residue.

The alloferons of the present invention have up to 30, preferably up to 20 and most preferable 5-13 amino acid residues.

Examples of alloferons of the present invention are summarized in Table 1.

Table 1. Amino acid sequences of alloferons (SEQ ID NOS 1-21), the homologous to alloferon fragment of influenza B virus precursor protein and general formula (1).

| Peptide | Position | | | | | | | | | | | | | | | |
|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 |
| Alloferon 1 | His | Gly | Val | Ser | Gly | His | Gly | — | Gln | — | His | Gly | Val | His | Gly | — |
| Alloferon 2 | — | Gly | Val | Ser | Gly | His | Gly | — | Gln | — | His | Gly | Val | His | Gly | — |
| Alloferon 3 | — | — | Val | Ser | Gly | His | Gly | — | Gln | — | His | Gly | Val | His | — | — |
| Alloferon 4 | — | — | — | Ser | Gly | His | Gly | — | Gln | — | His | Gly | Val | — | — | — |
| Alloferon 5 | Pro | Ser | Leu | Thr | Gly | His | Gly | — | Phe | — | His | Gly | Val | Tyr | Asp | — |
| Alloferon 6 | Phe | Ile | Val | Ser | Ala | His | Gly | — | Asp | — | His | Gly | Val | — | — | — |
| Alloferon 7 | — | — | — | — | Thr | His | Gly | — | Gln | — | His | Gly | Val | — | — | — |
| Alloferon 8 | — | — | — | — | — | His | Gly | — | — | — | His | Gly | Val | His | Gly | — |
| Alloferon 9 | — | Leu | Ala | Ser | Leu | His | Gly | — | Gln | — | His | Gly | Val | — | — | — |
| Alloferon 10 | Cys | Val | Val | Thr | Gly | His | Gly | — | Ser | — | His | Gly | Val | Phe | Val | — |
| Alloferon 11 | — | — | Ile | Ser | Gly | His | Gly | — | Gln | — | His | Gly | Val | Pro | — | — |
| Alloferon 12 | — | — | — | Cys | Gly | His | Gly | — | Asn | — | His | Gly | Val | His | — | — |
| Alloferon 13 | Ile | Val | Ala | Arg | Ile | His | Gly | — | Gln | Asn | His | Gly | Val | — | — | — |
| Alloferon 14 | — | — | — | — | — | His | Gly | Ser | Asp | Gly | His | Gly | Val | Gln | His | Gly |
| Alloferon 15 | — | — | — | Phe | Gly | His | Gly | — | — | — | His | Gly | Val | — | — | — |
| Alloferon 16 | — | — | — | — | — | His | Gly | — | Asn | — | His | Gly | Val | Leu | Ala | — |
| Alloferon 17 | His | Gly | Asp | Ser | Gly | His | Gly | — | Gln | — | His | Gly | Val | Asp | — | — |
| Alloferon 18 | — | — | — | — | — | His | Gly | — | — | — | His | Gly | Val | Pro | Leu | — |
| Alloferon 19 | — | — | — | Ser | Gly | His | Gly | — | Ala | Val | His | Gly | Val | Met | — | — |
| Alloferon 20 | Tyr | Ala | Met | Ser | Gly | His | Gly | — | — | — | His | Gly | Val | Phe | Ile | — |
| Influenza virus B precursor (positions 377–387) | His | Gly | Tyr | Thr | Ser | His | Gly | | Ala | | His | Gly | Val | | | |
| general formula (1) | | | | | $X_1$ | His | Gly | | $X_2$ | | His | Gly | Val | $X_3$ | | |

The chemical structure of alloferons has no similarity with interferons, other known cytokines and interferon inducers as well as any other materials of medical importance. The chemical structure of alloferons and the mode of biological activity are also quite different of those of arylphorin isolated from Calliphora and demonstrating immunologic and antitumor activity as it is disclosed in EP 0 320 528 A1. Alloferons preferably have a molecular mass close to 1200 Da and belong to the unique peptide family which has not been described so far. Calliphora arylphorin has a molecular mass of about 500 000 Da (Naumann U. and Scheller K. Biochem. Biophys. Res. Communications, 1991, 177, p. 963-971) and is proposed to be used as an adjuvant in the course of specific vaccination and specific stimulation of antibody-dependent T-lymphocytes antitumor activity as it is disclosed in EP 0 320 528 A1. No data concerning a possible effect of arylphorin on the natural killer cell activity and interferon synthesis are available up to now.

Alloferons are linear peptides having a unique amino acid sequence represented by the general formula as follows (SEQ ID NO:31):

$X_1$-His-Gly-$X_2$-His-Gly-Val-$X_3$

Alloferons 1 and 2 are natural peptides isolated from the blood of bacteria challenged larvae of an insect, *Calliphora vicina* in the course of purposeful screening of cytokine-like materials able to stimulate cytotoxic activity of mammalian natural killer cells. Alloferons 3 and 4 are truncated forms of alloferon 1, which were chemically synthesized in order to determine possible biologically active modifications of the natural prototype molecule.

Comparative study of the effect of alloferon 1-4 on the cytotoxic activity of lymphocytes demonstrated that all of them are bioactive molecules. See Example 5. This makes possible to distinguish conservative (functionally important) and variable parts of the alloferon structure. Alloferons 5-20 are examples represented to show preferred modifications of variable fragments of the basic structure of alloferon.

A data base search did not reveal peptides of natural origin or bioactive synthetic peptides having close similarity to the alloferon structure. Therefore alloferons are believed to belong to a new family of bioactive peptides. Nevertheless, alloferons have, to certain extent, structural analogy with fragments of some functionally important proteins. For example, alloferon 1 has 63% identity with fragment 377-387 of the influenza virus B hemagglutinin precursor. Hemagglutinin is known to be a key membranotropic protein of the virus envelope responsible for the integration with the cell membrane of the host.

Alloferon 1 was used as a prototype molecule in the course of the development of the invention. Alloferon 1 is a linear peptide having a molecular mass of 1265 Da consisting of 13 amino acids. See Table 1. A comparison with alloferons 2-4 allows to determine functionally important elements of the structure of alloferon, which are necessary for its efficacy as a stimulant of NK cell's cytotoxicity and, other activities, and to predict possible structural modifications, which do not change the biological activity of the peptide.

Comparison of alloferon 1 with the structure of alloferons 2-4 shows that the presence of the fragment Ser-Gly-His-Gly-Gln-His-Gly-Val (SEQ ID NO: 4) is sufficient to conserve the biological activity as since all the peptides exhibit similar activities in NK cell cytotoxicity test. Therefore, this fragment or a part of the fragment represents the core conservative structure in alloferon sequences. Positions 1-3 in the alloferon 1 molecule can be missing or can be replaced by one or more amino acids.

Furthermore, a comparison with the homologous fragment of the influenza virus hemagglutinin reveals that positions 4 and 5, represented in the alloferon 1 sequence by amino acids serin (Ser) and glycin (Gly), can be replaced by some other amino acid preferably chosen from the group of aliphatic, aromatic or heterocyclic amino acids. For instance, serin can be replaced by threonin (Thr) and glycin by serin.

Thus, the available data reveals that the first five amino acids in the alloferon 1 sequence are a variable fragment which can be absent or contain at least one amino acid. Therefore, this fragment is marked in the alloferon structural formula (1) as $X_1$. Advantageously, $X_1$ is Selected from the group consisting of nothing, His-Gly-Val-Ser-Gly-, Gly-Val-Ser-Gly-, Val-Ser-Gly-, Ser-Gly-, Pro-Ser-Leu-Thr-Gly-, Phe-Ile-Val-Ser-Ala-, Thr-, Leu-Ala-Ser-Leu-, Cys-Val-Val-Thr-Gly-, Ile-Ser-Gly-, Cys-Gly-, Ile-Val-Ala-Arg-Ile-, Phe-Gly-, His-Gly-Asp-Ser-Gly-, Ser-Gly- and Tyr-Ala-Met-Ser-Gly- (SEQ ID NOS 22-30).

Similarly, positions 14-15 in the alloferon 1 molecule can be missing or can be replaced by a sequence of one or more amino acids. Therefore, this fragment is marked in the alloferon structural formula (1) as $X_3$. Advantageously, $X_3$ is selected from the group consisting of nothing, -His-Gly, -His, -Tyr-Asp, -Phe-Val, -Pro, -Gln-His-Gly, -Leu-Ala, -Asp, -Pro-Leu, -Met and -Phe-Ile.

Moreover, comparison of alloferon and the corresponding hemagglutinin fragment reveals that position 9, occupied in the alloferon molecule by glutamin, is also variable and glutamin can be replaced by some other amino acid, for example, by alanin. Consequently, position 9 of the alloferon structural formula (1) is marked as $X_2$ which can be a peptide bond linking Gly and His or contain not less then 1 amino acid, preferably 0-3 amino acids, more preferably 0-2 amino acids and most preferable 1 amino acid, in particular -Gln-.

Advantageously, $X_2$ is selected from the group consisting of a peptide bond, -Gln-, -Phe-, -Asp-, -Ser-, -Asn-, -Ala-, -Gln-Asn-, -Ala-Val- and -Ser-Asp-Gly-.

Incorporation of the alloferon sequence into a larger molecule such as a carrier protein without significant alteration of the biological activity of the alloferon is also possible. Thus, the present invention also relates to chemical compounds such as peptides or proteins comprising an amino acid sequence having the above general formula (1), provided that the peptide or protein is not naturally occurring, and in particular not the influenza virus B precursor.

Complex immunological, pharmacological and toxicological studies summarized in the examples below demonstrate a range of useful properties of alloferons. The obtained data show that alloferon is a new cytokine-like peptide. The mode of action of alloferon comprises stimulation of nonself or aberrant self recognition of cells and lysis by the cytotoxic lymphocytes as well as induction of interferon synthesis. Therefore, alloferon is useful as immunomodulatory medicine to correct a deficiency in the production of interferons and activity of natural killer cells, treatment of viral, oncological and other diseases dependent on the said deficiency. Alloferon is practically nontoxic, has no teratogenic, embryotoxic or mutagenic properties as it is shown in advanced preclinical studies.

The experimentally established properties of alloferon 1 are summarized in Table 2.

TABLE 2

Experimentally proved pharmacological activities of alloferon 1.

| Activity | Effective in vivo dose (mg/kg body mass) or in vitro concentration (ng/ml) | Medical use |
| --- | --- | --- |
| 1. Stimulation of mouse spleen lymphocytes' cytotoxic activity | 0.05–50 ng/ml | Therapy of infectious and oncological diseases |
| 2. Stimulation of mice' resistance to the influenza virus A infection | 1.25 mg/kg | Influenza therapy |
| 3. Stimulation of mice' resistance to the influenza virus B infection | 1.25 mg/kg | Influenza therapy |
| 4. Interferon synthesis induction in mice | 0.125–1.25 mg/kg | Therapy and prophylaxis of viral and oncological diseases |
| 5. Stimulation of human peripheral blood lymphocytes' cytotoxic activity | 0.0005–500 ng/ml | Therapy and prophylaxis of viral and oncological diseases |
| 6. Stimulation of peripheral blood lymphocytes' cytotoxic activity in cancer patients | 5 ng/ml | Adjuvant therapy of cancer |

The pharmacological activity spectrum, in general, corresponds to known properties of interferon-alpha concerning the influence on the cytotoxic activity of natural killer cells and antiviral resistance. In that aspect, alloferon can be characterized as interferon-alpha functional analog. The mode of action of alloferon, regarding in vitro stimulation of NK cells cytotoxic activity, is observed at very low concentrations—about 1 picogram/ml ($10^{-9}$ g/ml). In that aspect alloferon is as active or more active as endogenous cytokines, interferons and interleukins.

Moreover, alloferon is able to induce, alone or in cooperation with interleukin 12, the synthesis of endogenic interferons, including interferon-gamma. Therefore, alloferon can be attributed to the group of interferon inducers.

Preclinical studies of the in vivo activity of alloferon show that it has potent antiviral activity when tested using as a model mice infected by human influenza virus. In this model wild type males were infected intranasally by a suspension of the human influenza virus and alloferon 1 was injected intraperitoneally one day before infection and then 1, 2, 4, 6 and 8 days after. Alloferon effectively protected mice from pulmonary lesions and death. Thus, alloferons are useful in the preparation of a pharmaceutical preparation for the treatment or prevention of viral infections.

Neither an acute nor a chronic toxicity of alloferon 1 was found in the course of in vivo and in vitro studies.

It is understood that the pharmaceutical preparations of the present invention may also comprise conventional additives like excipients or carriers. The preparations may be administered to the patient by intranasal, enteral, such as oral or rectal, and parenteral, such as intraperitoneal, intramuscular, intravenous or subcutaneous route. The preparations may be administered in dosage forms such as intranasal dropping solutions, sprays, liposomes, capsules, tablets and suppositories. For parenteral use the pharmaceutically active components are preferably in the form of an injectable solution.

Thus, alloferons are useful in the treatment or prophylaxis of various infectious or oncological diseases where improvement of innate immunity, including interferon system and natural cell mediated cytotoxicity, can have therapeutic significance. The examples of conditions under which alloferons application is prospective comprise influenza virus and other respiratory viral infections, viral hepatitis, AIDS and AIDS relevant secondary infections and oncological conditions, acute and chronic leukemia and other cancers where interferon treatment efficacy is proved, fungal systemic infections sensitive to the interferon treatment etc.

In spite of a certain similarity in biological activity (NK cell cytotoxic activity stimulation, indirect antiviral activity), alloferons differ very much of interferons in terms of structure and mode of action. Thus, interferons are glycoproteins with molecular mass ranging from 17 000 to 80 000 daltons. Glycosilation of amino acid chain is a necessary condition of interferon functional activity as well as their tissue and species specificity. Alloferon is a preferably nonglycosilated oligopeptide having molecular mass of preferably about 1265 Da, 13-60 times less then interferons molecular masses. The amino acid sequence of alloferon has no similarity with any fragment of interferon sequences. There are essential differences between alloferons and interferons in functional aspect as well. Thus, alloferon induces the production of endogenic interferons and promotes in this way a cascade of defense responses mediated by interferons. Exogenous interferon application may rather suppress endogenic interferon synthesis by means of negative feedback mechanism.

The peptides of the present invention can be isolated from natural sources or synthesized by known methods. The peptides of this invention can also be produced by recombinant DNA techniques. Thus, the invention comprises cultivating a cell host previously transformed with a suitable vector containing a DNA sequence, e.g. a cDNA encoding a peptide sequence including any of the peptides of this invention, said DNA sequence being placed under the control of a promoter and followed by termination signals recognized by the cell host machinery such as to authorize the expression said DNA sequence of said peptide sequence, and recovering the peptide sought from the expression of products of the cell culture. Advantageous host cells belong to Lactobacillus strains, *E. coli*, Agrobacterium or Bacillus strains. Alternatively the peptides can be easily produced by well known chemical synthesis.

The invention is further illustrated by the following examples:

EXAMPLE 1

Isolation of Alloferons from Insect Blood, Structural Characterization and Chemical Synthesis Alloferons were initially discovered in the blood of the immunized (bacteria challenged) insect, blowfly *Calliphora vicina*. Postfeeding *C. vicina* larvae maintained in the laboratory conditions as described (Chernysh S. I., Simonenko N. P., Numata H. Appl. Entomol. Zool., 1995, Vol. 30, No. 3, p. 498-499) were bacteria challenged by the pricking off cuticle with a needle soaked in a suspension of heat-killed *Escherichia coli* and *Micrococcus luteus* cells. The hemolymph of septically injured larvae was collected, centrifuged and applied onto a Sep-Pak C18 chromatographic column (Waters Co). The column was washed with 0.05% trifluoroacetic acid. Then the target materials were eluted with 50% acetonitril acidified with 0.05% trifluoroacetic acid. The eluted composition was lyophilized and used to stepwise chromatographic purification of the active principle. The biological activity of the fractions was monitored during purification steps using mouse spleen lymphocytes as cytotoxic cells and H3-uridine labeled K562 cancer cells as a target.

As a result of the purification steps, two close oligopeptides demonstrated potent immunomudulatory activity and referred to as alloferons 1 and 2 were isolated from the primary composition and chemically characterized. The amino acid sequence of the peptides was determined using an automated Edman degradation method on a model 473A sequenator (Applied Biosystems). The structure of alloferon 1 and 2 was determined as follows:

```
His-Gly-Val-Ser-Gly-his-Gly-Gln-Val-His-Gly           (alloferon 1) (SEQ ID NO: 1)

Gly-Val-Ser-Gly-His-Gly-Gln-His-Gly-Val-His-Gly   (alloferon 2) (SEQ ID NO: 2)
```

The peptides were further analyzed by MALDI-TOF ionozation mass spectrometry on a Bruker (Bremen) BIFLEX matrix-assisted laser desorption time-of-flight mass spectrometer and their molecular masses were experimentally determined as 1265 Da (alloferon 1) and 1126 Da (alloferon 2). The masses of alloferon 1 and 2 deduced from the amino acid sequencing data and the masses determined by mass spectrometry are in good agreement confirming that alloferon 1 and 2 are linear peptides having no posttranslational modifications.

Alloferon 1 was selected as a prototype molecule for biological and preclinical studies. In order to get sufficient amount of alloferon 1 for the further experimentation, it was chemically synthesized by means of solid phase peptide synthesis technology (Neimark J. and J.-P. Brian, Peptide Research, 1993, vol.6, p. 219) The peptide purification protocol included two major steps. First step was performed on the Sep-Pak Vac columns with C18 sorbent (Waters) by means of the column elution by 40% acetonitril acidified by 0.05% trifluoroacetic acid. Finally the peptide was purified to homogeneity using a Beckman Gold System chromatograph equipped with an Aquapore ODS Prep 10 C18 (100×10 mm, Brownlee) column in the linear gradient of 0.05% trifluoroacetic acid and acidified acetonitril (0-20% acetonitril during 40 min under flow rate 2.5 ml/min and detector wave length 225 nm). The peptide purity was confirmed by MALDI-TOF mass spectrometry. The amino acid sequence's accuracy was confirmed by microsequencing.

Truncated forms of alloferon 1, alloferons 3 and 4, were synthesized, purified and controlled in the same way as described for alloferon 1.

EXAMPLE 2

Effect of Alloferon 1 on the Cytotoxic Activity of Mouse Spleen Lymphocytes

To analyze the effect of alloferon on the mouse spleen lymphocytes' cytotoxic activity, the standard cytotoxicity assay was used (Hashimoto J. and Sudo E., Gann, 1971, vol. 62, 139-145; Filatova N. A., Malygin A. M., Goryunova L. B., Fel V. Ya. and Khavinson V. K., Tsitologia, 1990, Vol. 32, No. 6, 652-658). H3-uridine labeled K562 human leukemia cells were used as targets for a cytotoxic lymphocytes' attack. Fresh spleen lymphocytes and target cells were co-incubated during 18 hours in the presence or absence of the preparation. Then the proportion of killed and normal target cells and the corresponding cytotoxicity indices were determined in control and experimental groups.

A typical result of the synthetic alloferon 1 stimulatory activity is shown in Table 3.

Alloferon administration to the incubation medium in a broad concentrations range (0.05-50 ng/ml) induced statistically significant amplification of the cytotoxic activity of natural killer cells against target tumor cells. A concentration of 500 ng/ml was not stimulatory. However, in that case the cytotoxic activity was not suppressed below the control level as well.

Therefore, even 10000-times excess of the minimum effective concentration was not harmful to the cytotoxic activity of NK cells.

Thus, alloferon efficiently stimulates the cytotoxic activity of mouse spleen lymphocytes at very low concentrations characteristic to specific cytokines such as interferon-alpha or interleukin 2 responsible for NK cells activation. At the same time, alloferon did not demonstrate immunosuppressive properties even under 10000-fold excess of the effective concentration.

TABLE 3 in vitro effect of alloferon 1 on the mouse spleen lymphocytes' cytotoxicity to K562 human leukemia cells

| Treatment | Concentration, ng/ml | Cytotoxicity index Average, % (n = 18) | % to control |
|---|---|---|---|
| Control | 0 | 21.3 ± 3.0 | 100 |
| Alloferon | 0.05 | 35.2 ± 4.0** | 165 |
| | 0.5 | 39.3 ± 3.9*** | 185 |
| | 5 | 34.3 ± 4.5** | 161 |
| | 50 | 37.2 ± 4.5** | 175 |
| | 500 | 20.3 ± 3.6 | 95 |

**P < 0.01;
***P < 0.001

EXAMPLE 3

Effect of Alloferon 1 on the Cytotoxic Activity of Human Peripheral Blood Lymphocytes The determination of the cytotoxicity index has been performed as described in Example 2. Human peripheral blood lymphocytes were released from fresh donor blood and purified of erythrocytes by centrifugation using the histopak 1077 solution (Sigma). After centrifugation the lymphocytes were resuspended in phosphate buffer, centrifuged and resuspended again in RPMI 1640 medium supplemented with RNAase. The lymphocytes were diluted up to $2 \times 10^6$ cells/ml and immediately used for the cytotoxicity analysis. Interferon-alpha 2b (Intron, Shering-Plough), a natural stimulant of NK cells' cytotoxic activity was used as a positive control.

The PBLs' cytotoxicity against K562 cancer cells was significantly increased when the preparation was added to the incubation medium in a concentration starting from 0.0005 nanogram/ml, however, the stimulatory activity reached a plato at a concentration of about 0.05 nanogram/ml (Table 4). Interferon-alpha 2b administered in a concentration of 5 ng/ml was less effective as compared to the alloferon administered in the optimal concentration rang of 0.05-0.5 ng/ml.

These experimental data demonstrate a strong stimulatory effect of alloferon on the in vitro cytotoxic activity of human peripheral blood lymphocytes directed to the lysis of tumor cells.

TABLE 4

Effect of alloferon and interferon-alpha 2b on the cytotoxicity of human periferal blood lymphocytes.

| Treatment | ng/ml Concentration, | Cytotoxicity index % | % to control |
|---|---|---|---|
| Control | 0 | 27.3 ± 7.3 | 100 |
| Interferon-alpha 2b | 5 | 64.3 ± 3.8 | 236*** |
| Alloferon | 0.0005 | 62.0 ± 6.4 | 227*** |
| | 0.005 | 73.8 ± 1.7 | 270*** |
| | 0.05 | 79.8 ± 5.0 | 292*** |
| | 0.5 | 79.8 ± 2.8 | 292*** |
| | 5 | 66.8 ± 7.2 | 245*** |
| | 50 | 68.0 ± 5.3 | 249*** |
| | 500 | 68.8 ± 4.4 | 252*** |

***P < 0.001

EXAMPLE 4

Comparative Study of Alloferon 1 and Interferon-alpha 2b Efficacy Variation Regarding Stimulation of the Cytotoxic Activity of Lymphocytes in the Population of Healthy Donors PBLs' cytotoxic activity was monitored in the random sampling of 17 healthy donors in order to evaluate diversity and correlation of the lymphocytes' responses to alloferon and interferon-alpha 2b stimulation. The cytotoxic activity was evaluated as described in Examples 2 and 3. Two kinds of target cells were used in the study simultaneously: the K562 cell line originated from erythromyeloid leukemia cells and the A431 cell line originated from the solid colorectal tumor. The proportion of lymphocytes and target cells (E/T ratio) in the trial was 20:1.

The data obtained are summarized in Table 5. Each figure in the Table comprises results of 6 cytotoxicity determinations. The data show significant variation of the cytotoxic activity of the lymphocytes in the control groups, particularly a different capacity to recognize and eliminate the target cells of different origin. Responses to the preparation's administration are also different. Nevertheless a clear correlation of the responses to the alloferon and interferon administration was found in most donors: donors positively responding to interferon in most cases also positively respond to alloferon and vice versa.

Generalized figures of the efficacy of two preparations calculated on the basis of the data in Table 5 are shown in Table 6. Most donors were responding to interferon (10 out of 17 donors) and alloferon (also 10 donors) by statistically approved increase of the cytotoxic activity against K562 or A431 targets. Responsivenesses to alloferon and interferon administration were in good correlation: 9 donors were equally responsive to both preparations and each one donor was selectively responsive to interferon or alloferon, respectively.

Thus, an analysis of the healthy donors' responsiveness shows that alloferon and interferon-alpha 2b possess similar efficacy in this model. Moreover, two preparations seem interchangeable as stimulants of the activity of cytotoxic lymphocytes in most although not all individuals.

TABLE 5

Effect of alloferon and interferon-alpha 2b
($K_{fin}$ = 5 ng/ml) on the cytotoxicity of
peripheral blood lymphocytes (PBL) in healthy donors
(lymphocyte:target ratio = 20:1).

| N° | Preparation | Cytotoxicity index, M ± m, % | | Statistically significant stimulation ($P \leq 0.05$) | |
|---|---|---|---|---|---|
| | | K562 | A431 | K562 | A431 |
| 1 | Control | 5.3 ± 4.4 | 53.8 ± 6.5 | | |
| | Interferon | 50.2 ± 1.6*** | 55.7 ± 8.6 | + | − |
| | Alloferon | 30.2 ± 5.5** | 83.7 ± 2.9** | + | + |
| 2 | Control | 14.2 ± 3.3 | −64.5 ± 40.6 | | |
| | Interferon | 50.2 ± 2.5*** | −88.3 ± 40.4 | + | − |
| | Alloferon | 39.8 ± 1..5*** | −86.7 ± 22.8 | + | − |
| 3 | Control | 29.8 ± 7.4 | −53.6 ± 19.9 | | |
| | Interferon | 21.8 ± 7.5 | 27.0 ± 6.5** | − | + |
| | Alloferon | 30.8 ± 6.8 | 39.7 ± 33*** | − | + |
| 4 | Control | 30.0 ± 2.9 | 83.8 ± 3.6 | | |
| | Interferon | 42.8 ± 2.4** | 89.5 ± 2.3 | + | − |
| | Alloferon | 45.4 ± 2.3*** | 91.2 ± 0.9 | + | − |
| 5 | Control | 43.3 ± 3.5 | −14.8 ± 8.3 | | |
| | Interferon | 64.2 ± 5.7*** | 35.4 ± 5.2*** | + | + |
| | Alloferon | 51.0 ± 1.7 | 24.4 ± 4.0** | − | + |
| 6 | Control | 41.7 ± 10.5 | 50.0 ± 5.7 | | |
| | Interferon | 30.5 ± 8.6 | 43.7 ± 5.0 | − | − |
| | Alloferon | 37.6 ± 10.2 | 53.7 ± 4.4 | − | − |
| 7 | Control | 40.3 ± 3.2 | 17.3 ± 5.5 | | |
| | Interferon | 58.2 ± 2.5** | 11.8 ± 8.3 | + | − |
| | Alloferon | 59.2 ± 5.2** | −10.2 ± 8.0 | + | − |
| 8 | Control | 23.0 ± 3.5 | −20.0 ± 6.3 | | |
| | Interferon | 19.2 ± 2.3 | 74.0 ± 2.7*** | − | + |
| | Alloferon | 29.2 ± 6.3 | 80.7 ± 1.8*** | − | + |
| 9 | Control | 6.2 ± 11.3 | 7.8 ± 15.6 | | |
| | Interferon | 25.0 ± 4.6 | 38.5 ± 3.4 | − | − |
| | Alloferon | 25.0 ± 12.3 | 24.5 ± 15.1 | − | − |
| 10 | Control | 34.3 ± 1.3 | 74.0 ± 4.5 | | |
| | Interferon | 51.8 ± 2.9** | 82.7 ± 1.9 | + | − |
| | Alloferon | 44.8 ± 3.5* | 88.4 ± 1.2** | + | + |
| 11 | Control | 57.0 ± 4.4 | 37.2 ± 6.7 | | |
| | Interferon | 52.0 ± 2.2 | 50.8 ± 9.2 | − | − |
| | Alloferon | 42.8 ± 5.9 | 46.5 ± 7.6 | − | − |
| 12 | Control | 61.8 ± 3.4 | 55.6 ± 4.9 | | |
| | Interferon | 71.8 ± 2.9* | 51.4 ± 3.6 | + | − |
| | Alloferon | 47.8 ± 4.1 | 56.4 ± 3.1 | − | − |
| 13 | Control | 44.0 ± 13.1 | 52.8 ± 6.5 | | |
| | Interferon | 62.7 ± 7.5 | 58.2 ± 6.1 | − | − |
| | Alloferon | 49.7 ± 3.9 | 54.8 ± 4.0 | − | − |
| 14 | Control | 30.2 ± 6.1 | −6.0 ± 8.1 | | |
| | Interferon | 14.7 ± 8.7 | 48.7 ± 4.5** | − | + |
| | Alloferon | 2.0 ± 4.2 | 49.8 ± 12.9** | − | + |
| 15 | Control | 16.8 ± 2.3 | 11.2 ± 6.8 | | |
| | Interferon | 2.2 ± 3.8 | 25.0 ± 5.7 | − | − |
| | Alloferon | 19.5 ± 6.8 | 27.7 ± 3.7 | − | − |
| 16 | Control | −3.5 ± 7.4 | 61.4 ± 7.1 | | |
| | Interferon | 5.0 ± 4.7 | 69.2 ± 2.1 | − | − |
| | Alloferon | 18.5 ± 1.7* | 68.7 ± 2.0 | + | − |
| 17 | Control | 23.3 ± 5.6 | 57.8 ± 4.1 | | |
| | Interferon | 29.0 ± 3.3 | 62.5 ± 1.7 | − | − |
| | Alloferon | 24.7 ± 4.0 | 64.3 ± 4.1 | − | − |

*$P < 0.05$;
**$P < 0.01$;
***$P < 0.001$

TABLE 6

Comparative characteristics of the efficacy of
alloferon and interferon-alpha 2b
regarding PBLs' cytotoxic activity stimulation
in the random sampling of healthy donors (from
the data of Table 5).

| Indicator | Interferon | Alloferon |
|---|---|---|
| Number of donors | 17 | |
| Positive responses* proportion (taking into account target specificity): | | |
| K562 | 7/17 = 41% | 6/17 = 35% |
| A431 | 4/17 = 24% | 6/17 = 35% |
| K562 or A531 | 10/17 = 59% | 10/17 = 59% |
| Positive responses* coincidence: | | |
| Interferon and alloferon sensitive donors | 9/17 = 53% | |
| Donors selectively sensitive to interferon | 1/17 = 6% | |
| Donors selectively sensitive to alloferon | 1/17 = 6% | |

*Positive response = statistically significant increase of lymphocyte cytotoxicity index

EXAMPLE 4

Comparative Study of the Efficacy Variation of Alloferon 1 and Interferon-alpha 2b Regarding Stimulation of the Lymphocytes' Cytotoxic Activity in the Random Sampling of Cancer Patients Blood samples from 18 patients with different malignancies have been tested according to the same protocol as healthy donors of Example 3. Results are shown in Table 7. Positive responses to alloferon treatment were registered in various patient groups, particularly those suffered by chronic and acute leucosis (5 of 9 cases). Positive responses were also detected in patients suffered by non-Hodgkin lymphoma (2 of 6 cases) and one lung cancer patient.

The proportion of individuals positively responding to interferon or alloferon was slightly decreased in cancer patients compared to healthy donors but also significant (56% and 50% of the total number, respectively). The correlation of responsiveness to interferon and alloferon was also weaker compared to healthy donors although evidential as well. According to the given test, alloferon seems to be an adequate replacement of injectable interferon in some part of cancer patients. However, assuming that alloferon not only mimics interferon activity but also stimulates the production of endogenic interferons, alloferon appears to be even more prospective as replacement of injectable interferon because of the expected double stimulation of the immune response via direct activation of natural cytotoxicity and induction of endogenic interferon synthesis.

TABLE 7

Effect of alloferon and interferon-alpha 2b on the
cytotoxicity of peripheral blood
lymphocytes (PBL) in cancer patients
(lymphocyte:target ratio = 20:1).

| | | | Cytotoxicity index, % | | Statistically significant stimulation ($P \leq 0.05$) | |
|---|---|---|---|---|---|---|
| N° | Diagnosis | Treatment | K562 | A431 | K562 | A431 |
| 1 | Chronic leucosis | Control | 11.2 ± 10.6 | −4.2 ± 8.7 | | |
| | | Interferon | −5.5 ± 7.9 | 11.7 ± 12.5 | − | − |
| | | Alloferon | −35.3 ± 5.4 | −9.0 ± 12.7 | − | − |
| 2 | Chronic leucosis | Control | 4.8 ± 5.4 | 37.0 ± 5.6 | | |
| | | Interferon | −10.7 ± 4.9 | 33.3 ± 9.0 | − | − |
| | | Alloferon | 1.3 ± 2.3 | 8.2 ± 8.3 | − | − |
| 3 | Chronic leucosis | Control | −8.3 ± 2.3 | −16.2 ± 10.6 | | |
| | | Interferon | −3.5 ± 4.0 | 33.5 ± 7.4** | − | + |
| | | Alloferon | −12.8 ± 3.7 | 26.2 ± 3.8** | − | + |
| 4 | Chronic leucosis | Control | −11.0 ± 3.6 | 28.2 ± 5.9 | | |
| | | Interferon | −9.2 ± 7.0 | 18.8 ± 4.3 | − | − |
| | | Alloferon | −1.5 ± 5.1 | 19.2 ± 6.3 | − | − |
| 5 | Chronic leucosis | Control | −23.0 ± 5.3 | 15.2 ± 8.3 | | |
| | | Interferon | −4.6 ± 9.6 | 46.0 ± 4.0** | − | + |
| | | Alloferon | −8.0 ± 18.8 | 42.5 ± 3.9** | − | + |
| 6 | Acute leucosis | Control | 42.3 ± 2.7 | 6.2 ± 16.5 | | |
| | | Interferon | 25.2 ± 4.0** | 43.5 ± 6.4* | − | + |
| | | Alloferon | 20.2 ± 6.8** | 48.5 ± 13.5* | − | + |
| 7 | Acute leucosis | Control | 29.2 ± 5.6 | −18.7 ± 14.6 | | |
| | | Interferon | 50.2 ± 2.3** | 24.8 ± 10.1* | + | + |
| | | Alloferon | 28.2 ± 2.6 | 20.0 ± 6.9* | − | + |
| 8 | Acute leucosis | Control | 15.2 ± 9.4 | 25.2 ± 6.5 | | |
| | | Interferon | 40.0 ± 3.4** | 17.8 ± 8.3 | + | − |
| | | Alloferon | 23.5 ± 5.5 | 40.4 ± 6.2 | − | − |
| 9 | Acute leucosis | Control | 23.5 ± 8.2 | −4.8 ± 9.0 | | |
| | | Interferon | 25.1 ± 4.6 | 51.5 ± 6.5*** | − | + |
| | | Alloferon | 13.8 ± 4.4 | 51.8 ± 4.8*** | − | + |

TABLE 7-continued

Effect of alloferon and interferon-alpha 2b on the cytotoxicity of peripheral blood lymphocytes (PBL) in cancer patients (lymphocyte:target ratio = 20:1).

| N° | Diagnosis | Treatment | Cytotoxicity index, % | | Statistically significant stimulation ($P \leq 0.05$) | |
|---|---|---|---|---|---|---|
| | | | K562 | A431 | K562 | A431 |
| 10 | Lung cancer | Control | 11.5 ± 3.7 | −7.2 ± 10.2 | | |
| | | Interferon | 27.2 ± 4.2** | 59.5 ± 3.9*** | + | + |
| | | Alloferon | −0.3 ± 6.1 | 55.5 ± 2.7*** | − | + |
| 11 | Uterus cancer | Control | 30.5 ± 1.3 | 93.3 ± 1.0 | | |
| | | Interferon | 50.8 ± 4.9*** | 93.5 ± 0.9 | + | − |
| | | Alloferon | 24.0 ± 4.4 | 94.3 ± 0.4 | − | − |
| 12 | Hodgkin lymphoma | Control | 22.2 ± 8.7 | 90.3 ± 0.95 | | |
| | | Interferon | 39.3 ± 4.9 | 95.2 ± 0.79** | − | + |
| | | Alloferon | 27.7 ± 4.8 | 90.2 ± 0.47 | − | − |
| 13 | Non-Hodgkin lymphoma | Control | 11.5 ± 6.4 | 82.8 ± 1.1 | | |
| | | Interferon | 13.8 ± 3.0 | 80.2 ± 2.0 | − | − |
| | | Alloferon | 17.7 ± 2.8 | 91.5 ± 0.8*** | − | + |
| 14 | Non-Hodgkin lymphoma | Control | 16.3 ± 9.6 | −40.0 ± 20.5 | | |
| | | Interferon | 31.2 ± 9.2 | 26.0 ± 8.9** | − | + |
| | | Alloferon | 36.7 ± 9.1 | 15.3 ± 4.8** | − | + |
| 15 | Non-Hodgkin lymphoma | Control | 19.2 ± 12.1 | 57.7 ± 4.4 | | |
| | | Interferon | 47.5 ± 6.6* | 62.2 ± 5.2 | + | − |
| | | Alloferon | 37.3 ± 4.7 | 64.0 ± 5.0 | − | − |
| 16 | Non-Hodgkin lymphoma | Control | 35.8 ± 8.3 | 47.2 ± 10.4 | | |
| | | Interferon | 43.2 ± 3.5 | 43.5 ± 4.4 | − | − |
| | | Alloferon | 37.3 ± 7.0 | 56.3 ± 4.4 | − | − |
| 17 | Non-Hodgkin lymphoma | Control | 49.4 ± 3.2 | 66.7 ± 6.2 | | |
| | | Interferon | 48.8 ± 3.5 | 67.0 ± 3.3 | − | − |
| | | Alloferon | 68.3 ± 4.6** | 64.3 ± 5.1 | + | − |
| 18 | Non-Hodgkin lymphoma | Control | 6.3 ± 14.9 | 29.8 ± 4.6 | | |
| | | Interferon | −3.0 ± 8.7 | 33.2 ± 7.4 | − | − |
| | | Alloferon | −10.7 ± 14.1 | 32.8 ± 9.2 | − | − |

*$P < 0.05$;
**$P < 0.01$;
***$P < 0.001$

TABLE 8

Comparative characteristics of the efficacy of alloferon and interferon-alpha 2b regarding PBLs' cytotoxic activity stimulation in the random sampling of cancer patients (from the data of Table 7).

| Indicator | Interferon | Alloferon |
|---|---|---|
| Number of donors | 18 | |
| Positive responses* proportion (taking into account target specificity): | | |
| K562 | 6/18 = 33% | 1/18 = 6% |
| A431 | 8/18 = 44% | 8/18 = 44% |
| K562 or A531 | 10/18 = 56% | 9/18 = 50% |
| Positive responses* coincidence: | | |
| Interferon and alloferon sensitive donors | 7/18 = 38% | |
| Donors selectively sensitive to interferon | 4/18 = 22% | |
| Donors selectively sensitive to alloferon | 2/18 = 11% | |

*Positive response = statistically significant increase of lymphocyte cytotoxicity index

EXAMPLE 5

Influence of Alloferon 1 Structural Analogs on the Cytotoxic Activity of Human Peripheral Blood Lymphocytes The activity of alloferon 1 analogs, alloferons 3 and 4, was investigated according to the protocols described in Examples 2 and 3. The mononuclear fraction isolated from the blood of healthy donors and target cell of the A431 cell line were co-incubated in the presence of one of the preparations: alloferon 1, alloferon 3, alloferon 4 or interferon-alpha 2b (positive control). The preparation's concentration in all cases was 5 ng/ml. Cytotoxicity index excess over the untreated control was used as the efficacy criterion.

The data of Table 9 demonstrate similar efficacy of alloferons 3 and 4 compared to alloferon 1 and interferon-alpha 2b.

Thus, the comparative analysis of the efficacy of alloferon 1 structural analogs, alloferons 3 and 4, shows that positions 1-4 and/or 14-15 in the alloferon 1 amino acid sequence (See Table 1) are unnecessary for it's specific pharmacological activity and, therefore, represent variable parts of the alloferon 1 structure which can be changed or replaced without activity loss.

TABLE 9

Effects of alloferons 1, 3 and 4 and interferon-alpha 2b on the cytotoxic activity of human peripheral blood lymphocytes against A431 tumor cells.

| Preparation | Experiments number | Average cytotoxicity index, M ± m, % | P |
|---|---|---|---|
| Control | 6 | −6.0 ± 8.1 | |
| Interferon | 6 | 48.7 ± 4.6 | <0.001 |
| Alloferon 1 | 4 | 49.8 ± 12.8 | <0.01 |
| Alloferon 3 | 6 | 60.2 ± 2.7 | <0.001 |
| Alloferon 4 | 5 | 60.8 ± 2.4 | <0.001 |

EXAMPLE 6

In vivo Antiviral Activity of Alloferon on Mice Infected by Human Influenza Virus A The antiviral activity of alloferon was investigated using the model of lethal infection of mice by the human influenza virus A. A suspension of the pathogenic to mice virus strain A/Aichi/2/68 (cerotype H3N2) was administered intranasally in a dose equal to 10 $LD_{50}$ doses to wild type males with body mass ranging from 20 to 22 g. Alloferon 1 dissolved in 0.5 ml of 0.9% NaCl was injected intraperitoneally one day before virus inoculation, then 1, 2, 4, 6 and 8 days after inoculation. The preparation was tested in two doses: 25 and 2.5 microgram per mouse (0.5 and 0.05 microgram/kg). Control mice were injected with an equal volume of the solvent. The mortality of the mice was monitored during 10 days after infection.

The data of Table 10 show significant decrease of post infection mortality in the group treated with 25 micrograms of alloferon. The 2.5 microgram dose was not effective.

TABLE 10

Alloferon antiviral activity in mice inoculated by human influenza virus A

| Treatment | Dosage, microgram per mouse | N | Mortality 10 days after virus inoculation N | % |
|---|---|---|---|---|
| Control | — | 20 | 14 | 70 |
| Alloferon | 2.5 | 20 | 13 | 65 |
| Alloferon | 25 | 20 | 5 | 25* |

*$P < 0.05$

Similar results were obtained in the experiment where the antiviral activity of alloferon was compared with that of remantadin. See Table 11. Remantadin (amantadine derivative) is one of the most powerful antiviral agents specifically effective against influenza virus A (Ershov F. I. Antiviral preparations, Medicina, Moscow, 1998, 187 pp). Alloferon was injected subcutaneously in a dose of 25 microgram one day before virus inoculation, then one hour before inoculation, then 1 and 2 days post infection. Remantadin in the dose 1000 microgram was given per os one day before virus inoculation, then one hour before inoculation, then 1, 2 and 3 days post infection.

Both alloferon and remantadin effectively protected most of the infected animals from lethal pulmonary lesions caused by the influenza virus. Remantadin appears to be slightly more effective in the case of influenza virus A infection, however it must be used in a significantly larger dosage (about 40 times higher) compared to the alloferon. Moreover, remantadin is known to be ineffective in the case of influenza virus B and other viral infections contrary to alloferon which is equally effective to A and B strains of the influenza virus.

TABLE 11

Antiviral activity of alloferon and remantadin in mice infected with human influenza virus A.

| Treatment | Dosage, microgram per mouse | N | Mortality 10 days after virus inoculation N | % |
|---|---|---|---|---|
| Control | — | 20 | 13 | 65 |
| Alloferon | 25 | 18 | 4 | 22* |
| Remantadin | 1000 | 19 | 1 | 5*** |

*$P < 0.05$;
***$P < 0.001$

EXAMPLE 7

In vivo Antiviral Activity of Alloferon on Mice Infected by Human Influenza Virus B The anti-virus B efficacy of alloferon was tested according to the protocol described in Example 6. Animals were intranasally inoculated with pathogenic to mouse Lee 1/40 human influenza virus B strain in doses equal to 3 and 30 $LD_{50}$. Ribavirin, 1-beta-D-ribofuranosyl-1,2,4,-triazole-3-carboxamide, an antiviral agent effective against various influenza virus strains (Liao H. J. and Stollar V. Antiviral Res., 1993, 22, 285; Ershov F. I. Antiviral preparations, Medicina, Moscow, 1998, 187 pp) was used as a positive control.

The results are shown in Table 12. The infection caused severe pneumonia with high mortality rate in both control groups, independent of the virus dosage. Ribavirin effectively protected mice inoculated with a lower virus dose (3 $LD_{50}$), however it was not effective against a higher virus dose (30 $LD_{50}$). At the same time, alloferon was equally effective in both cases. Therefore alloferon demonstrated better antiviral efficacy compared to the known antiviral agent, ribavirin. Moreover, alloferon is effective at a dose approximately 10 times less of ribavirin's therapeutic dose.

TABLE 12

Antiviral activity of alloferon and ribavirin in mice infected with human influenza virus B.

| Treatment | Virus dose ($LD_{50}$ equivalents) | Animals number | Mortality 10 days after virus inoculation Number | % |
|---|---|---|---|---|
| Control | 30 | 13 | 10 | 77 |
| | 3 | 10 | 8 | 80 |
| Ribavirin, 250 microgram | 30 | 10 | 6 | 60 |
| | 3 | 10 | 0 | 0*** |
| Alloferon, 25 microgram | 30 | 10 | 2 | 20** |
| | 3 | 10 | 0 | 0*** |

**$P < 0.01$
***$P < 0.001$

EXAMPLE 8

In vivo Effects of Alloferon on the Interferon Synthesis in Mice

In order to investigate the possible mode of alloferon's antiviral activity, the in vivo effect of the preparation on the interferon synthesis in mice was studied. The interferon concentration in the blood serum of alloferon treated and control (untreated) animals was determined using as a model a monolayer of L-929 cells. Vesicular stomatitis virus (Indiana strain) has been used as a test-virus in a dose 100 times exceeding the 50% cytopathogenic doses. One unit of interferon activity is expressed as a value reciprocal to the mouse serum dilution protecting 50% L-929 cells against the cytotoxicity of the test-virus. Cycloferon was used as a positive control. Cycloferon is an interferon inducer which belongs to the chemical group of acridanons (Ershov F. I. Antiviral preparations, Medicina, Moscow, 1998, 187 pp). Alloferon or cycloferon were injected intraperitoneally in a dose of 25 microgram and 500 microgram, respectively.

The results of two series of the experiment are summarized in Table 13. In each series the experimental groups comprised 4 animals. Blood samples were collected from each animal, then individual serum aliquots were combined and used for the interferon determination. Alloferon stimulated statistically significant the growth of the interferon concentration with a maximum efficacy reached 24 h post treatment.

TABLE 13

Effect of alloferon on the interferon synthesis in mice.

| Treatment | Hours | Animals number | Experiments number | Interferon titre, Arbitrary units |
|---|---|---|---|---|
| Control |  | 8 |  | 15 ± 5 |
| Cycloferon, | 4 | 8 | 2 | 95 ± 45 |
| 500 microgram | 24 | 8 | 2 | 49 ± 3.8* |
| Alloferon, | 2 | 8 | 2 | 31 ± 13.8 |
| 25 microgram | 4 | 8 | 2 | 21 ± 3.7 |
|  | 24 | 8 | 2 | 71 ± 16.2* |

*$P < 0.05$

Another example of the in vivo effect of alloferon on the interferon synthesis in mice is shown in the Table 14. The method was the same as in the previous experiment except that alloferon was administered subcutaneously and individual blood samples were analyzed separately. Both alloferon and cycloferon stimulated the interferon production in short-term prospect, 6 hours after treatment. During 24 hours the titre of interferon returned to the control level both in alloferon and cycloferon treated animals.

Thus, the data above confirm that alloferon injection has an in vivo interferon inducing activity on the level similar to those of cycloferon, a known interferon inducer. The length of the stimulatory effect can range from 6 to 24 hours or more, depending, probably, on the physiological state of the animal and way of administration. Compared to traditional chemical interferon inducers such as cycloferon alloferon has the advantage to be effective at a much lower dosage (about 20 times less).

TABLE 14

Short-term effect of alloferon on the interferon synthesis in mice.

| Treatment | Time, h | Animals number | Interferon titre, Arbitrary units |
|---|---|---|---|
| Control |  | 7 | 7.1 ± 1.8 |
| Cycloferon, | 6 | 7 | 32.9 ± 10.7* |
| 500 microgram | 24 | 7 | 11.4 ± 2.8 |
| Alloferon, | 6 | 8 | 40.6 ± 11.4* |
| 25 microgram | 24 | 8 | 14.4 ± 4.3 |

*$P < 0.05$

EXAMPLE 9

Alloferon Toxicity Evaluation

The toxicity of alloferon was tested using a panel of in vitro and in vivo models. See Table 15. No signs of acute or chronic toxicity, allergenic activity, embriotoxicity or harmful effect on the reproductive function in animal and microbial models, or a cytotoxicity in human in vitro models were registered so far. Therefore it is concluded that alloferon has very low toxicity or is a practically nontoxic material.

TABLE 15

Summary of alloferon safety analysis

| Activity | Method | Results | Conclusion |
|---|---|---|---|
| Acute toxicity | Single subcutaneous and intragastric administration, 500-6000 mg/kg in mice and 300-5000 mg/kg in rats | Mortality was not registered in any dose including highest dose. No changes in animal growth, feeding, macroscopical structure of brain, inner and endocrine organs as well as skin and subcutaneous cellular tissue around injection place were found at the any dosage. | Toxicometric data are positive. Toxic/therapeutic dose ratio >35700 times in rats and >42800 times in mice. |
| Subacute and chronic toxicity in rats | 0.2, 2 and 20 mg/kg once a day during 90 days | None animal died during 90 day period. Analysis of animal growth, feeding, rectal temperature, ophthalmological (mucous surfaces state and eye morphometry), neuropsychological (excitability threshold, spontaneous locomotors activity) cardiovascular (systolic arterial pressure, heart beating rate, ECG) liver (hexenal sleep), kidney (urine composition, phenol red excretion), hematological (hemogram, leukocyte formula, coagulogram) indices, biochemical indices of peripheral blood (proteinemia, urea, creatinin, | Alloferon has no toxic effects on the rats under long term daily administration at therapeutic dose and doses 10 and 100 times exceeding |

TABLE 15-continued

Summary of alloferon safety analysis

| Activity | Method | Results | Conclusion |
|---|---|---|---|
| | | glucose, lipids, cholesterol, bilirubin, enzymatic activity, electrolyte composition), blood forming indices, pathomorphological and histological (heart, lungs, tracheas, stomach, pancreas, epithelial tissues, thymus, liver, spleen, kidney, adrenal, brain, testicles, ovary) data did not show negative changes in the organism's functions. | therapeutic. |
| Allergenic activity in guinea pigs | Anaphylactic shock | No signs of anaphylaxy were found at therapeutic dosage. Minimal response (short term unrest, nose scratch and quickened breath) was registered in 1 male but 12 guinea pigs which obtained 10-fold therapeutic dose. | Alloferon has no detectable allergenic activity. |
| | Immune complexes reaction | The reaction was not found under alloferon therapeutic and 10-fold administration | |
| | Indirect reaction of fat cells degranulation | Fat cells degranulation rate was not changed under alloferon therapeutic and 10-fold administration | |
| | Conjunctive probe | The reaction was not found under alloferon therapeutic and 10-fold administration | |
| | Reaction of delayed hypersensitivity | The reaction was not found under alloferon therapeutic and 10-fold administration | |
| Embriotoxicity and influence on the reproductive function | Subcutaneous injection 1.5 and 15 mg/kg into pregnant rats | Alloferon administration did not cause negative effects in the course of embryonic development and postnatal development in offsprings as well as alterations of male and female reproductive function | Alloferon has no embryotoxic activity as well influence on the reproductive activity in rats |
| Mutagenic activity | Dominant lethal mutations in the mouse germ cells | Alloferon in the dose 15 mg/kg did not induce dominant lethal mutations in the mouse germ cells | Alloferon has no mutagenic and potential cancerogenic activity |
| | Chromosome aberrations in the mouse bone marrow cells | Alloferon in the single dose 0.5 and 15 mg/kg and fivefold dose 0.5 mg/kg did not induce chromosome aberrations in the mouse bone marrow cells | |
| | Ames test | Alloferon in the concentration range 0.1-1000 microgram/Petri dish did not induce gene mutations in 3 test line of *Salmonella tiphimurium*. | |
| | DNA SOS-reparation | Alloferon has no DNA-damaging activity in the *E. coli* test-line PQ37 | |

The invention claimed is:

1. A method of manufacturing a composition having immunomodulatory activity, comprising combining a peptide of up to 30 amino acid residues comprising the amino acid sequence of any one of SEQ ID NOS: 1-4, or a pharmaceutically active salt or ether of the peptide with a conventional additive.

2. The method of claim 1, wherein said peptide comprises SEQ ID NO:4.

3. The method of claim 1, wherein the peptide consists of less than 30 amino acids.

4. The method of claim 1, wherein the composition is a pharmaceutical that exhibits at least one of interferon inducing activity, antiviral activity, antitumor activity or stimulation of the cytotoxic activity of human or animal lymphocytes.

5. The method of claim 1, wherein the composition is a pharmaceutical useful for the treatment or prophylaxis of at least one of an immune deficient condition, an infection, a viral infection, a fungal systemic infection, and an oncological disease.

6. A method of treating a condition, comprising administering to a subject in need thereof an effective amount of the immunomodulatory composition made by the method of claim 1.

7. The method of claim 6 wherein said condition is selected from the group consisting of an immune deficient condition, an infection and an oncology.

* * * * *

SEQUENCE LISTING

<160> NUMBER OF SEQ ID NOS: 32

<210> SEQ ID NO 1
<211> LENGTH: 13
<212> TYPE: PRT
<213> ORGANISM: Calliphora vicina

<400> SEQUENCE: 1

His Gly Val Ser Gly His Gly Gln His Gly Val His Gly
1               5                   10

<210> SEQ ID NO 2
<211> LENGTH: 12
<212> TYPE: PRT
<213> ORGANISM: Calliphora vicina

<400> SEQUENCE: 2

Gly Val Ser Gly His Gly Gln His Gly Val His Gly
1               5                   10

-continued

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      alloferon 3

<400> SEQUENCE: 3

Val Ser Gly His Gly Gln His Gly Val His
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      alloferon 4

<400> SEQUENCE: 4

Ser Gly His Gly Gln His Gly Val
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      alloferon 5

<400> SEQUENCE: 5

Pro Ser Leu Thr Gly His Gly Phe His Gly Val Tyr Asp
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      alloferon 6

<400> SEQUENCE: 6

Phe Ile Val Ser Ala His Gly Asp His Gly Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      alloferon 7

<400> SEQUENCE: 7

Thr His Gly Gln His Gly Val
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      alloferon 8
```

```
<400> SEQUENCE: 8

His Gly His Gly Val His Gly
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
                        alloferon 9

<400> SEQUENCE: 9

Leu Ala Ser Leu His Gly Gln His Gly Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
                        alloferon 10

<400> SEQUENCE: 10

Cys Val Val Thr Gly His Gly Ser His Gly Val Phe Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
                        alloferon 11

<400> SEQUENCE: 11

Ile Ser Gly His Gly Gln His Gly Val Pro
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
                        alloferon 12

<400> SEQUENCE: 12

Cys Gly His Gly Asn His Gly Val His
1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
                        alloferon 13

<400> SEQUENCE: 13

Ile Val Ala Arg Ile His Gly Gln Asn His Gly Val
1               5                   10

<210> SEQ ID NO 14
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
                        alloferon 14

<400> SEQUENCE: 14

His Gly Ser Asp Gly His Gly Val Gln His Gly
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
                        alloferon 15

<400> SEQUENCE: 15

Phe Gly His Gly His Gly Val
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
                        alloferon 16

<400> SEQUENCE: 16

His Gly Asn His Gly Val Leu Ala
1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
                        alloferon 17

<400> SEQUENCE: 17

His Gly Asp Ser Gly His Gly Gln His Gly Val Asp
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
                        alloferon 18

<400> SEQUENCE: 18

His Gly His Gly Val Pro Leu
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
                        alloferon 19

<400> SEQUENCE: 19

Ser Gly His Gly Ala Val His Gly Val Met
```

-continued

```
1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
                        alloferon 20

<400> SEQUENCE: 20

Tyr Ala Met Ser Gly His Gly His Gly Val Phe Ile
1               5                  10

<210> SEQ ID NO 21
<211> LENGTH: 11
<212> TYPE: PRT
<213> ORGANISM: Influenza virus B

<400> SEQUENCE: 21

His Gly Tyr Thr Ser His Gly Ala His Gly Val
1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 22

His Gly Val Ser Gly
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 23

Gly Val Ser Gly
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 24

Pro Ser Leu Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 25
```

-continued

```
Phe Ile Val Ser Ala
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 26

Leu Ala Ser Leu
1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 27

Cys Val Val Thr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 28

Ile Val Ala Arg Ile
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 29

His Gly Asp Ser Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 30

Tyr Ala Met Ser Gly
1               5

<210> SEQ ID NO 31
<211> LENGTH: 80
<212> TYPE: PRT
<213> ORGANISM: Artificial Sequence
```

```
<220> FEATURE:
<223> OTHER INFORMATION: Description of Artificial Sequence: General
                        structural formula sequence
<220> FEATURE:
<221> NAME/KEY: MOD_RES
<222> LOCATION: (1)..(25)
<223> OTHER INFORMATION: Any amino acid or not present; this range may
                        encompass 0-25 residues with the proviso that
                        total sequence length does not exceed 30
                        residues
<220> FEATURE:
<221> NAME/KEY: MOD_RES
<222> LOCATION: (28)..(52)
<223> OTHER INFORMATION: Any amino acid or not present; this range may
                        encompass 0-25 residues with the proviso that
                        total sequence length does not exceed 30
                        residues
<220> FEATURE:
<221> NAME/KEY: MOD_RES
<222> LOCATION: (56)..(80)
<223> OTHER INFORMATION: Any amino acid or not present; this range may
                        encompass 0-25 residues with the proviso that
                        total sequence length does not exceed 30
                        residues

<400> SEQUENCE: 31

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa His Gly Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa His Gly Val Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
 65                  70                  75                  80

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
                        peptide fragment

<400> SEQUENCE: 32

Ser Gly His Gly Gln His Gly Val
 1               5
```